US008053218B2

(12) United States Patent
Chevreux et al.

(10) Patent No.: US 8,053,218 B2
(45) Date of Patent: Nov. 8, 2011

(54) GENE STS 18

(75) Inventors: Bastian Chevreux, Rheinfelden (DE); Anne F. Mayer, Basel (CH); Anja Meury, Basel (CH); Nigel J. Mouncey, Binningen (CH); Masako Shinjoh, Kanagawa (JP)

(73) Assignee: DSM IP Assets B.V., Heerlen (NL)

( * ) Notice: Subject to any disclaimer, the term of this patent is extended or adjusted under 35 U.S.C. 154(b) by 453 days.

(21) Appl. No.: 11/883,782

(22) PCT Filed: Feb. 10, 2006

(86) PCT No.: PCT/EP2006/001209
§ 371 (c)(1),
(2), (4) Date: Sep. 28, 2007

(87) PCT Pub. No.: WO2006/084714
PCT Pub. Date: Aug. 17, 2006

(65) Prior Publication Data
US 2008/0213852 A1    Sep. 4, 2008

(30) Foreign Application Priority Data

Feb. 11, 2005 (EP) .................................... 05405066
Feb. 11, 2005 (EP) .................................... 05405084

(51) Int. Cl.
*C12P 17/04* (2006.01)
(52) U.S. Cl. ........................................................ 435/126
(58) Field of Classification Search .................... 435/126
See application file for complete search history.

(56) References Cited

U.S. PATENT DOCUMENTS

| 2006/0035349 A1 | 2/2006 | Hoshino et al. |
| 2006/0121582 A1 | 6/2006 | Hoshino et al. |
| 2007/0161093 A1 | 7/2007 | Hoshino et al. |

OTHER PUBLICATIONS

International Search Report for related Appln. No. PCT/EP2006/001209, completed Jul. 2006.
Prust et al. "Complete genome sequence of the acetic acid bacterium *Gluconobacter oxydans*" Nature Biotechnology, vol. 23, No. 2, pp. 195-200 (Jan. 2005).

*Primary Examiner* — Tekchand Saidha
(74) *Attorney, Agent, or Firm* — Nixon & Vanderhye P.C.

(57) ABSTRACT

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of the polynucleotides and polypeptides as biotechnological tools in the production of Vitamin C from microorganisms, whereby a modification of the polynucleotides and/or encoded polypeptides has a direct or indirect impact on yield, production, and/or efficiency of production of the fermentation product in the microorganism. Also included are methods/processes of using the polynucleotides and modified polynucleotide sequences to transform host microorganisms. The invention also relates to genetically engineered microorganisms and their use for the direct production of Vitamin C.

15 Claims, No Drawings

GENE STS 18

This application is a U.S. national stage of International Patent Application No. PCT/EP2006/001209, filed 10 Feb. 2006, which designated the U.S. and claims priority benefit of EP 05405084.4, filed 11 Feb. 2005, and EP 05405066.1, filed 11 Feb. 2005; the entire contents of each of which are hereby incorporated by reference.

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of Vitamin C from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for the direct production of Vitamin C.

Vitamin C is one of very important and indispensable nutrient factors for human beings. Vitamin C is also used in animal feed even though some farm animals can synthesize it in their own body.

For the past 70 years, Vitamin C has been produced industrially from D-glucose by the well-known Reichstein method. All steps in this process are chemical except for one (the conversion of D-sorbitol to L-sorbose), which is carried out by microbial conversion. Since its initial implementation for industrial production of Vitamin C, several chemical and technical modifications have been used to improve the efficiency of the Reichstein method. Recent developments of Vitamin C production are summarized in Ullmann's Encyclopedia of Industrial Chemistry, 5$^{th}$ Edition, Vol. A27 (1996), pp. 547ff.

Different intermediate steps of Vitamin C production have been performed with the help of microorganisms or enzymes isolated therefrom. Thus, 2-keto-L-gluconic acid (2-KGA), an intermediate compound that can be chemically converted into Vitamin C by means of an alkaline rearrangement reaction, may be produced by a fermentation process starting from L-sorbose or D-sorbitol, by means of strains belonging e.g. to the *Ketogulonicigenium* or *Gluconobacter* genera, or by an alternative fermentation process starting from D-glucose, by means of recombinant strains belonging to the *Gluconobacter* or *Pantoea* genera.

Current chemical production methods for Vitamin C have some undesirable characteristics such as high-energy consumption and use of large quantities of organic and inorganic solvents. Therefore, over the past decades, other approaches to manufacture Vitamin C using microbial conversions, which would be more economical as well as ecological, have been investigated.

Direct Vitamin C production from a number of substrates including D-sorbitol, L-sorbose and L-sorbosone has been reported in several microorganisms, such as algae, yeast and acetic acid bacteria, using different cultivation methods. Examples of known bacteria able to directly produce Vitamin C include, for instance, strains from the genera of *Gluconobacter, Gluconacetobacter, Acetobacter, Ketogulonicigenium, Pantoea, Pseudomonas* or *Escherichia*. Examples of known yeast or algae include, e.g., *Candida, Saccharomyces, Zygosaccharomyces, Schizosaccharomyces, Kluyveromyces* or *Chlorella*.

Microorganisms able to assimilate D-sorbitol for growth usually possess enzymes able to oxidize this compound into a universal assimilation substrate such as D-fructose. Also microorganisms able to grow on L-sorbose possess an enzyme, NAD(P)H-dependent L-sorbose reductase, which is able to reduce this compound to D-sorbitol, which is then further oxidized into D-fructose. D-fructose is an excellent substrate for the growth of many microorganisms, after it has been phosphorylated by means of a D-fructose kinase.

For instance, in the case of acetic acid bacteria, which are obligate aerobe, gram-negative microorganisms belonging to the genus *Acetobacter, Gluconobacter*, and *Gluconacetobacter*, these microorganisms are able to transport D-sorbitol into the cytosol and convert it into D-fructose by means of a cytosolic NAD-dependent D-sorbitol dehydrogenase. Some individual strains, such as *Gluconobacter oxydans* IFO 3292, and IFO 3293, are able as well to transport L-sorbose into the cytosol and reduce it to D-sorbitol by means of a cytosolic NAD(P)H-dependent L-sorbose reductase, which then is further oxidized into D-fructose. In these bacteria, the Embden-Meyerhof-Parnas pathway, as well as the tricarboxylic acid cycle are not fully active, and the main pathway channeling sugars into the central metabolism is the pentose phosphate pathway. D-fructose-6-phosphate, obtained from D-fructose by a phosphorylation reaction enters the pentose phosphate pathway, being further metabolized and producing reducing power in the form of NAD(P)H and tricarboxylic compounds necessary for growth and maintenance.

Acetic acid bacteria are well known for their ability to incompletely oxidize different substrates such as alcohols, sugars, sugar alcohols and aldehydes. These processes are generally known as oxidative fermentations or incomplete oxidations, and they have been well established for a long time in the food and chemical industry, especially in vinegar and in L-sorbose production. A useful product known to be obtained from incomplete oxidations of D-sorbitol or L-sorbose using strains belonging to the *Gluconobacter* genus is 2-KGA.

Acetic acid bacteria accomplish these incomplete oxidation reactions by means of different dehydrogenases located either in the periplasmic space, on the periplasmic membrane as well as in the cytoplasm. Different co-factors are employed by the different dehydrogenases, the most common being PQQ and FAD for membrane-bound or periplasmic enzymes, and NAD/NADP for cytoplasmic enzymes.

While all products of these oxidation reactions diffuse back to the external aqueous environment through the outer membrane, some of them can be passively or actively transported into the cell and be further used in metabolic pathways responsible for growth and energy formation. Inside the cell, oxidized products can many times be reduced back to their original substrate by means of reductases, and then be channeled back to the central metabolism.

Proteins, in particular transporters, that are active in the transportation of sugar such as e.g. glucose, sugar alcohols and related compounds across the cellular membrane are herein referred to as being involved in the Sugar Transport System. Such proteins are abbreviated herein as STS proteins.

STS proteins are in general membrane-bound or are associated to membrane-bound structures and are functional as single proteins or as subunits in protein complexes such as permeases or active transporters. STS proteins are known to be responsible for selectively facilitating, assisting or enabling the transport of compounds such as sugars, sugar alcohols, sugar ketones or sugar aldehydes across the cellular or periplasmatic membrane.

STS proteins can be divided into three types on the basis of their mechanisms. The first class of transporters uses energy from the proton-motive force to transport molecules against a concentration gradient. These symport and antiport systems couple the movement of two different molecules across the membrane (via permeases having two separate binding sites for the two different molecules); in symport, both molecules are transported in the same direction, while in antiport, one molecule is imported while the other is exported.

The second class of transporters, the phosphotransferase system (PTS), is energized by the transfer of a high-energy phosphate group from phosphoenolpyruvate, through various protein components, to the substrate which is phosphorylated upon import as its phosphoester form.

The third class of transporters couples the hydrolysis of ATP to substrate translocation. These systems are termed the ATP-binding cassette (ABC) type transporters. The ABC-transport system consists of a substrate specific binding protein which is located in the periplasm in gram-negative bacteria or which is membrane associated in gram-positive bacteria, an integral membrane domain and a cytoplasmic-facing ATP hydrolyzing domain.

A more detailed description of membrane transport systems can be found in: Bamberg, E. et al (1993) "Charge transport of ion pumps on lipid bilayer membranes", Q. Rev. Biophys. 26:1-25; Findlay, J. B. C. (1991) "Structure and function of membrane transport systems", Curr. Opin. Struct. Biol. 1:804-810; Higgins, C. F. (1992) "ABC transporters from microorganism to man" Ann. Rev. Cell Biol. 8:67-113; Gennis, R. B. (1989) "Pores, channels and transporters" in: Biomembranes, Molecular Structure and Function, Springer, Heidelberg, p. 270-322; Nikaido, H. & Saier H. (1992). "Transport proteins in bacteria: common themes in their design" Science 258:936-942.

An object of the present invention is to improve the yields and or productivity of Vitamin C production.

Surprisingly, it has now been found that STS proteins or subunits of such proteins having activity towards or which are involved in the transportation of compounds across cellular membranes play an important role in the biotechnological production of Vitamin C.

In one embodiment, STS proteins of the present invention are selected from transferases [EC 2], preferably transferases transferring phosphorus-containing groups [EC 2.7], more preferably phosphotransferases with an alcohol group as acceptor [EC 2.7.1] and phosphotransferases with a nitrogenous group as acceptor [EC 2.7.3], most preferably protein-np-phosphohistidine-sugar phosphotransferase [EC 2.7.1.69] and phosphoenolpyruvate-protein phosphotransferase [EC 2.7.3.9] or from hydrolases [EC 3], preferably hydrolases acting on acid anhydrides [EC 3.6].

Furthermore, the STS proteins of the present invention may be selected from sugar transporters and/or sugar alcohol transporters, preferably transporter proteins and periplasmic binding/transfer proteins, more preferably, periplasmic sorbitol-binding proteins, periplasmic solute-binding proteins, periplasmic D-allose-binding proteins, trehalose/maltose ABC transporters including subunits like membrane components, mannitol/sorbitol ABC-type transporter including subunits like MtlK ATPase or membrane (MtlG or MtlF) components, and proteins involved in PTS including PtsI enzyme I, Hpr protein, enzyme IIA$^{Man}$, P-loop ATPase protein family or Hpr kinases.

In particular, it has now been found that STS proteins encoded by polynucleotides having a nucleotide sequence that hybridizes preferably under highly stringent conditions to a sequence shown in SEQ ID NO:1 play an important role in the biotechnological production of Vitamin C. It has also been found, that by genetically altering the expression level of nucleotides according to the invention in a microorganism capable of directly producing Vitamin C, such as for example Gluconobacter, the direct fermentation of Vitamin C by said microorganism can be even greatly improved.

Consequently, the invention relates to a polynucleotide selected from the group consisting of:

(a) polynucleotides encoding a polypeptide comprising the amino acid sequence according to SEQ ID NO:2;

(b) polynucleotides comprising the nucleotide sequence according to SEQ ID NO:1;

(c) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4;

(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of a sugar transporter and/or sugar alcohol transporter, preferably STS 18 activity;

(e) polynucleotides the complementary strand of which hybridizes under stringent conditions to a polynucleotide as defined in any one of (a) to (d) and which encode a sugar transporter and/or sugar alcohol transporter, preferably a STS 18 polypeptide; and (f) polynucleotides which are at least 70%, such as 85, 90 or 95% identical to a polynucleotide as defined in any one of (a) to (d) and which encode a sugar transporter and/or sugar alcohol transporter, preferably a STS 18 polypeptide;

or the complementary strand of such a polynucleotide.

The STS protein as isolated from *Gluconobacter oxydans* DSM 17078 shown in SEQ ID NO:2 and described herein was found to be a particularly useful STS protein, since it appeared that it performs a crucial function in the direct Vitamin C production in microorganisms, in particular in bacteria, such as acetic acid bacteria, such as *Gluconobacter, Acetobacter* and *Gluconacetobacter*. Accordingly, the invention relates to a polynucleotide encoding a polypeptide according to SEQ ID NO:2. This protein may be encoded by a nucleotide sequence as shown in SEQ ID NO:1. The invention therefore also relates to polynucleotides comprising the nucleotide sequence according to SEQ ID NO:1.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). From the searches, the STS 18 polynucleotide according to SEQ ID NO:1 was annotated as encoding a periplasmic sorbitol-binding protein.

A nucleic acid according to the invention may be obtained by nucleic acid amplification using cDNA, mRNA or alternatively, genomic DNA, as a template and appropriate oligonucleotide primers such as the nucleotide primers according to SEQ ID NO:3 and SEQ ID NO:4 according to standard PCR amplification techniques. The nucleic acid thus amplified may be cloned into an appropriate vector and characterized by DNA sequence analysis.

The template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

Accordingly, the invention relates to polynucleotides comprising a nucleotide sequence obtainable by nucleic acid amplification such as polymerase chain reaction, using DNA such as genomic DNA from a microorganism as a template and a primer set according to SEQ ID NO:3 and SEQ ID NO:4.

The invention also relates to polynucleotides comprising a nucleotide sequence encoding a fragment or derivative of a polypeptide encoded by a polynucleotide as described herein wherein in said derivative one or more amino acid residues are conservatively substituted compared to said polypeptide, and said fragment or derivative has the activity of a STS polypeptide, preferably a STS 18 polypeptide.

The invention also relates to polynucleotides the complementary strand of which hybridizes under stringent conditions to a polynucleotide as defined herein and which encode a STS polypeptide, preferably a STS 18 polypeptide.

The invention also relates to polynucleotides which are at least 70% identical to a polynucleotide as defined herein and which encode a STS polypeptide; and the invention also relates to polynucleotides being the complementary strand of a polynucleotide as defined herein above.

The invention also relates to microorganisms wherein the activity of a STS polypeptide, preferably a STS 18 polypeptide, is enhanced and/or improved so that the yield of Vitamin C which is directly produced from D-sorbitol or L-sorbose is increased. This may be accomplished, for example, by transferring a polynucleotide according to the invention into a recombinant or non-recombinant microorganism that may or may not contain an endogenous equivalent of the STS 18 gene.

The skilled person will know how to enhance and/or improve the activity of a STS protein, preferably a STS 18 protein. Such may be for instance accomplished by either genetically modifying the host organism in such a way that it produces more or more stable copies of the STS protein, preferably the STS 18 protein, than the wild type organism or by increasing the specific activity of the STS protein, preferably the STS 18 protein.

In the following description, procedures are detailed to achieve this goal, i.e. the increase in the yield and/or production of Vitamin C which is which is directly produced from D-sorbitol or L-sorbose by increasing the activity of a STS 18 protein. These procedures apply mutatis mutandis for other STS proteins.

Modifications in order to have the organism produce more copies of the STS 18 gene, i.e. overexpressing the gene, and/or protein may include the use of a strong promoter, or the mutation (e.g. insertion, deletion or point mutation) of (parts of) the STS 18 gene or its regulatory elements. It may also involve the insertion of multiple copies of the gene into a suitable microorganism. An increase in the specific activity of an STS 18 protein may also be accomplished by methods known in the art. Such methods may include the mutation (e.g. insertion, deletion or point mutation) of (parts of) the STS 18 gene. A gene is said to be "overexpressed" if the level of transcription of said gene is enhanced in comparison to the wild type gene. This may be measured by for instance Northern blot analysis quantifying the amount of mRNA as an indication for gene expression. As used herein, a gene is overexpressed if the amount of generated mRNA is increased by at least 1%, 2%, 5% 10%, 25%, 50%, 75%, 100%, 200% or even more than 500%, compared to the amount of mRNA generated from a wild-type gene.

Also known in the art are methods of increasing the activity of a given protein by contacting the STS 18 protein with specific enhancers or other substances that specifically interact with the STS 18 protein. In order to identify such specific enhancers, the STS 18 protein may be expressed and tested for activity in the presence of compounds suspected to enhance the activity of the STS 18 protein. The activity of the STS 18 protein may also be increased by stabilizing the messenger RNA encoding STS 18. Such methods are also known in the art, see for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

The invention may be performed in any microorganism carrying a STS 18 gene or homologue thereof. Suitable microorganisms may be selected from the group consisting of yeast, algae and bacteria, either as wild type strains, mutant strains derived by classic mutagenesis and selection methods or as recombinant strains. Examples of such yeast may be, e.g., *Candida*, *Saccharomyces*, *Zygosaccharomyces*, *Schizosaccharomyces*, or *Kluyveromyces*. An example of such algae may be, e.g., *Chlorella*. Examples of such bacteria may be, e.g., *Gluconobacter*, *Acetobacter*, *Gluconacetobacter*, *Ketogulonicigenium*, *Pantoea*, *Pseudomonas*, such as, e.g., *Pseudomonas putida*, and *Escherichia*, such as, e.g., *Escherichia coli*. Preferred are *Gluconobacter* or *Acetobacter aceti*, such as for instance *G. oxydans*, *G. cerinus*, *G. frateurii*, *A. aceti* subsp. *xylinum* or *A. aceti* subsp. *orleanus*, preferably *G. oxydans* DSM 17078. *Gluconobacter oxydans* DSM 17078 (formerly known as *Gluconobacter oxydans* N44-1) has been deposited at Deutsche Sammlung von Mikroorganismen und Zellkulturen (DSMZ), Mascheroder Weg 1B, D-38124 Braunschweig, Germany according to the Budapest Treaty on 26, Jan. 2005.

Microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Jusohonmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateuri* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N 44-1 as another example of a preferred bacterium is a derivative of the strain IFO 3293 and is described in Sugisawa et al., Agric. Biol. Chem. 54: 1201-1209, 1990.

A microorganism as of the present invention may carry further modifications either on the DNA or protein level (see above), as long as such modification has a direct impact on the yield, production and/or efficiency of the direct production of Vitamin C from substrates like e.g. D-sorbitol or L-sorbose. Such further modifications may for instance affect other genes encoding STS proteins as described above, in particular genes encoding membrane-bound L-sorbosone dehydrogenases, such as L-sorbosone dehydrogenase SNDHai, or membrane-bound PQQ bound D-sorbitol dehydrogenases. Methods of performing such modifications are known in the art, with some examples further described herein. For the use of SNDHai for direct production of vitamin C as well as the nucleotide and amino acid sequence thereof we refer to WO 2005/017159 which is incorporated herein by reference.

In accordance with a further object of the present invention there is provided the use of a polynucleotide as defined above or a microorganism which is genetically engineered using such polynucleotides in the production of Vitamin C.

The invention also relates to processes for the expression of endogenous genes in a microorganism, to processes for the production of polypeptides as defined above in a microorganism and to processes for the production of microorganisms capable of producing Vitamin C. All these processes may comprise the step of altering a microorganism, wherein "altering" as used herein encompasses the process for "genetically altering" or "altering the composition of the cell culture media and/or methods used for culturing" in such a way that the yield and/or productivity of the fermentation product can be improved compared to the wild-type organism. As used herein, "improved yield of Vitamin C" means an increase of at least 5%, 10%, 25%, 30%, 40%, 50%, 75%, 100%, 200% or even more than 500%, compared to a wild-type microorganism, i.e. a microorganism which is not genetically altered.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

In accordance with still another aspect of the invention there is provided a process for the production of Vitamin C by direct fermentation.

In particular, the present invention provides a process for the direct production of Vitamin C comprising converting a substrate into Vitamin C. This may for instance be done in a medium comprising a microorganism, which may be a resting or a growing microorganism, preferably a resting microorganism.

Several substrates maybe used as a carbon source in a process of the present invention, i.e. a process for direct conversion of a given substrate into Vitamin C such as e.g. mentioned above. Particularly suited carbon sources are those that are easily obtainable from the D-glucose or D-sorbitol metabolization pathway such as, for example, D-glucose, D-sorbitol, L-sorbose, L-sorbosone, 2-keto-L-gluconate, D-gluconate, 2-keto-D-gluconate or 2,5-diketo-gluconate.

Preferably, the substrate is selected from for instance D-glucose, D-sorbitol, L-sorbose or L-sorbosone, more preferably from D-glucose, D-sorbitol or L-sorbose, and most preferably from D-sorbitol, L-sorbose or L-sorbosone. The term "substrate" and "production substrate" in connection with the above process using a microorganism is used interchangeably herein.

A medium as used herein for the above process using a microorganism may be any suitable medium for the production of Vitamin C. Typically, the medium is an aqueous medium comprising for instance salts, substrate(s), and a certain pH. The medium in which the substrate is converted into Vitamin C is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into desired products such as Vitamin C. Preferably, resting cells are used for the production of Vitamin C.

The term "direct fermentation", "direct production", "direct conversion" and the like is intended to mean that a microorganism is capable of the conversion of a certain substrate into the specified product by means of one or more biological conversion steps, without the need of any additional chemical conversion step. For instance, the term "direct conversion of D-sorbitol into Vitamin C" is intended to describe a process wherein a microorganism is producing Vitamin C and wherein D-sorbitol is offered as a carbon source without the need of an intermediate chemical conversion step. A single microorganism capable of directly fermenting Vitamin C is preferred. Said microorganism is cultured under conditions which allow such conversion from the substrate as defined above.

In connection with the above process using a microorganism it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). A particular reference is made to Urbance et al., IJSEM (2001) vol 51:1059-1070, with a corrective notification on IJSEM (2001) vol 51:1231-1233, describing the taxonomically reclassification of *G. oxydans* DSM 4025 as *Ketogulonicigenium vulgare*.

As used herein, resting cells refer to cells of a microorganism which are for instance viable but not actively growing, or which are growing at low specific growth rates, for instance, growth rates that are lower than 0.02 $h^{-1}$, preferably lower than 0.01 $h^{-1}$. Cells which show the above growth rates are said to be in a "resting cell mode".

The process of the present invention as above using a microorganism may be performed in different steps or phases: preferably, the microorganism is cultured in a first step (also referred to as step (a) or growth phase) under conditions which enable growth. This phase is terminated by changing of the conditions such that the growth rate of the microorganism is reduced leading to resting cells, also referred to as step (b), followed by the production of Vitamin C from the substrate using the (b), also referred to as production phase.

Growth and production phase as performed in the above process using a microorganism may be performed in the same vessel, i.e., only one vessel, or in two or more different vessels, with an optional cell separation step between the two phases. The produced Vitamin C can be recovered from the cells by any suitable means. Recovering means for instance that the produced Vitamin C may be separated from the production medium. Optionally, the thus produced Vitamin C may be further processed.

For the purpose of the present invention relating to the above process using a microorganism, the terms "growth phase", "growing step", "growth step" and "growth period" are used interchangeably herein. The same applies for the terms "production phase", "production step", "production period".

One way of performing the above process using a microorganism as of the present invention may be a process wherein the microorganism is grown in a first vessel, the so-called growth vessel, as a source for the resting cells, and at least part of the cells are transferred to a second vessel, the so-called production vessel. The conditions in the production vessel may be such that the cells transferred from the growth vessel become resting cells as defined above, Vitamin C is produced in the second vessel and recovered therefrom.

In connection with the above process using a microorganism, in one aspect, the growing step can be performed in an aqueous medium, i.e. the growth medium, supplemented with appropriate nutrients for growth under aerobic conditions. The cultivation may be conducted, for instance, in batch, fed-batch, semi-continuous or continuous mode. The cultivation period may vary depending on for instance the host, pH, temperature and nutrient medium to be used, and may be for instance about 10 h to about 10 days, preferably about 1 to about 10 days, more preferably about 1 to about 5 days when run in batch or fed-batch mode, depending on the microorganism. If the cells are grown in continuous mode, the residence time may be for instance from about 2 to about 100 h, preferably from about 2 to about 50 h, depending on the microorganism. If the microorganism is selected from bacteria, the cultivation may be conducted for instance at a pH of about 3.0 to about 9.0, preferably about 4.0 to about 9.0, more preferably about 4.0 to about 8.0, even more preferably about 5.0 to about 8.0. If algae or yeast are used, the cultivation may be conducted, for instance, at a pH below about 7.0, preferably below about 6.0, more preferably below about 5.5, and most preferably below about 5.0. A suitable temperature range for carrying out the cultivation using bacteria may be for instance from about 13° C. to about 40° C., preferably from about 18° C. to about 37° C., more preferably from about 13° C. to about 36° C., and most preferably from about 18° C. to about 33° C. If algae or yeast are used, a suitable temperature range for carrying out the cultivation may be for instance from about 15° C. to about 40° C., preferably from about 20° C. to about 45° C., more preferably from about 25° C. to about 40° C., even more preferably from about 25° C. to about 38° C., and most preferably from about 30° C. to about 38° C. The culture medium for growth usually may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, sucrose, and ethanol, preferably L-sorbose, D-glucose, D-sorbitol, D-mannitol, glycerol and ethanol; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium, usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as D-sorbitol, L-sorbose, or D-glucose, in such a way that they convert these substrates directly into Vitamin C. Incubation can be done in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing Vitamin C. Alternatively, incubation can be done in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride.

In connection with the above process using a microorganism, in the growth phase the specific growth rates are for instance at least $0.02\ h^{-1}$. For cells growing in batch, fed-batch or semi-continuous mode, the growth rate depends on for instance the composition of the growth medium, pH, temperature, and the like. In general, the growth rates may be for instance in a range from about 0.05 to about $0.2\ h^{-1}$, preferably from about 0.06 to about $0.15\ h^{-1}$, and most preferably from about 0.07 to about $0.13\ h^{-1}$.

In another aspect of the above process using a microorganism, resting cells may be provided by cultivation of the respective microorganism on agar plates thus serving as growth vessel, using essentially the same conditions, e.g., cultivation period, pH, temperature, nutrient medium as described above, with the addition of agar agar.

In connection with the above process using a microorganism, if the growth and production phase are performed in two separate vessels, then the cells from the growth phase may be harvested or concentrated and transferred to a second vessel, the so-called production vessel. This vessel may contain an aqueous medium supplemented with any applicable production substrate that can be converted to Vitamin C by the cells. Cells from the growth vessel can be harvested or concentrated by any suitable operation, such as for instance centrifugation, membrane crossflow ultrafiltration or microfiltration, filtration, decantation, flocculation. The cells thus obtained may also be transferred to the production vessel in the form of the original broth from the growth vessel, without being harvested, concentrated or washed, i.e. in the form of a cell suspension. In a preferred embodiment, the cells are transferred from the growth vessel to the production vessel in the form of a cell suspension without any washing or isolating step in-between.

Thus, in a preferred embodiment of the above process using a microorganism step (a) and (c) of the process of the present invention as described above are not separated by any washing and/or separation step.

In connection with the above process using a microorganism, if the growth and production phase are performed in the same vessel, cells may be grown under appropriate conditions to the desired cell density followed by a replacement of the growth medium with the production medium containing the production substrate. Such replacement may be, for instance, the feeding of production medium to the vessel at the same time and rate as the withdrawal or harvesting of supernatant from the vessel. To keep the resting cells in the vessel, operations for cell recycling or retention may be used, such as for instance cell recycling steps. Such recycling steps, for instance, include but are not limited to methods using centrifuges, filters, membrane crossflow microfiltration of ultrafiltration steps, membrane reactors, flocculation, or cell immobilization in appropriate porous, non-porous or polymeric matrixes. After a transition phase, the vessel is brought to process conditions under which the cells are in a resting cell mode as defined above, and the production substrate is efficiently converted into Vitamin C.

The aqueous medium in the production vessel as used for the production step in connection with the above process using a microorganism, hereinafter called production medium, may contain only the production substrate(s) to be converted into Vitamin C, or may contain for instance additional inorganic salts, e.g., sodium chloride, calcium chloride, magnesium sulfate, manganese sulfate, potassium phosphate, calcium phosphate, and calcium carbonate. The production medium may also contain digestible nitrogen sources such as for instance organic substances, e.g., peptone, yeast extract, urea, amino acids, and corn steep liquor, and inorganic substances, e.g. ammonia, ammonium sulfate, and sodium nitrate, at such concentrations that the cells are kept in a resting cell mode as defined above. The medium may be with or without urea and/or corn steep liquor and/or baker's yeast. The production step may be conducted for instance in batch, fed-batch, semi-continuous or continuous mode. In case of fed-batch, semi-continuous or continuous mode, both cells from the growth vessel and production medium can be fed continuously or intermittently to the production vessel at appropriate feed rates. Alternatively, only production medium may be fed continuously or intermittently to the production vessel, while the cells coming from the growth vessel are transferred at once to the production vessel. The cells coming from the growth vessel may be used as a cell suspension within the production vessel or may be used as for instance flocculated or immobilized cells in any solid phase such as porous or polymeric matrixes. The production period, defined as the period elapsed between the entrance of the substrate into the production vessel and the harvest of the supernatant containing Vitamin C, the so-called harvest stream, can vary depending for instance on the kind and concentration of cells, pH, temperature and nutrient medium to be used, and is preferably about 2 to about 100 h. The pH and temperature can be different from the pH and temperature of the growth step, but is essentially the same as for the growth step.

In a preferred embodiment of the above process using a microorganism, the production step is conducted in continuous mode, meaning that a first feed stream containing the cells from the growth vessel and a second feed stream containing the substrate is fed continuously or intermittently to the production vessel. The first stream may either contain only the cells isolated/separated from the growth medium or a cell suspension, coming directly from the growth step, i.e. cells suspended in growth medium, without any intermediate step of cell separation, washing and/or isolating. The second feed stream as herein defined may include all other feed streams necessary for the operation of the production step, e.g. the production medium comprising the substrate in the form of one or several different streams, water for dilution, and base for pH control.

In connection with the above process using a microorganism, when both streams are fed continuously, the ratio of the feed rate of the first stream to feed rate of the second stream may vary between about 0.01 and about 10, preferably between about 0.01 and about 5, most preferably between about 0.02 and about 2. This ratio is dependent on the concentration of cells and substrate in the first and second stream, respectively.

Another way of performing the process as above using a microorganism of the present invention may be a process using a certain cell density of resting cells in the production vessel. The cell density is measured as absorbance units (optical density) at 600 nm by methods known to the skilled person. In a preferred embodiment, the cell density in the production step is at least about 10, more preferably between about 10 and about 200, even more preferably between about 15 and about 200, even more preferably between about 15 to about 120, and most preferably between about 20 and about 120.

In connection with the above process using a microorganism, in order to keep the cells in the production vessel at the desired cell density during the production phase as performed, for instance, in continuous or semi-continuous mode, any means known in the art may be used, such as for instance cell recycling by centrifugation, filtration, membrane crossflow ultrafiltration of microfiltration, decantation, flocculation, cell retention in the vessel by membrane devices or cell immobilization. Further, in case the production step is performed in continuous or semi-continuous mode and cells are continuously or intermittently fed from the growth vessel, the cell density in the production vessel may be kept at a constant level by, for instance, harvesting an amount of cells from the production vessel corresponding to the amount of cells being fed from the growth vessel.

In connection with the above process using a microorganism, the produced Vitamin C contained in the so-called harvest stream is recovered/harvested from the production vessel. The harvest stream may include, for instance, cell-free or cell-containing aqueous solution coming from the production vessel, which contains Vitamin C as a result of the conversion of production substrate by the resting cells in the production vessel. Cells still present in the harvest stream may be separated from the Vitamin C by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

In a further aspect, the process of the present invention may be combined with further steps of separation and/or purification of the produced Vitamin C from other components contained in the harvest stream, i.e., so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Vitamin C may be further purified as the free acid form or any of its known salt forms by means of operations such as for instance treatment with activated carbon, ion exchange, adsorption and elution, concentration, crystallization, filtration and drying. Specifically, a first separation of Vitamin C from other components in the harvest stream might be performed by any suitable combination or repetition of, for instance, the following methods: two- or three-compartment electrodialysis, bipolar membrane electrodialysis, reverse osmosis or adsorption on, for instance, ion exchange resins or non-ionic resins. If the resulting form of Vitamin C is a salt of L-ascorbic acid, conversion of the salt form into the free acid form may be performed by for instance bipolar membrane electrodialysis, ion exchange, simulated moving bed chromatographic techniques, and the like. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. Vitamin C. The product thus obtained may further be isolated in a manner such as, e.g. by concentration, crystallization, precipitation, washing and drying of the crystals and/or further purified by, for instance, treatment with activated carbon, ion exchange and/or re-crystallization.

In a preferred embodiment, Vitamin C is purified from the harvest stream by a series of downstream processing steps as described above without having to be transferred to a non-aqueous solution at any time of this processing, i.e. all steps are performed in an aqueous environment. Such preferred downstream processing procedure may include for instance the concentration of the harvest stream coming from the production vessel by means of two- or three-compartment electrodialysis, conversion of Vitamin C in its salt form present in the concentrated solution into its acid form by means of bipolar membrane electrodialysis and/or ion exchange, purification by methods such as for instance treatment with activated carbon, ion exchange or non-ionic resins, followed by a further concentration step and crystallization. These crystals can be separated, washed and dried. If necessary, the crystals may be again re-solubilized in water, treated with activated carbon and/or ion exchange resins and recrystallized. These crystals can then be separated, washed and dried.

Advantageous embodiments of the invention become evident from the dependent claims. These and other aspects and embodiments of the present invention should be apparent to those skilled in the art from the teachings herein.

The sequence of the gene comprising a nucleotide sequence according to SEQ ID NO:1 encoding a STS 18 protein was determined by sequencing a genomic clone obtained from *Gluconobacter oxydans* DSM 17078.

The invention also relates to a polynucleotide encoding at least a biologically active fragment or derivative of a STS 18 polypeptide as shown in SEQ ID NO:2.

As used herein, "biologically active fragment or derivative" means a polypeptide which retains essentially the same biological function or activity as the polypeptide shown in SEQ ID NO:2. Examples of biological activity may for instance be enzymatic activity, signaling activity or antibody reactivity. The term "same biological function" or "functional equivalent" as used herein means that the protein has essentially the same biological activity, e.g. enzymatic, signaling or antibody reactivity, as a polypeptide shown in SEQ ID NO:2.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide", "gene" and "recombinant gene" refer to nucleic acid molecules which may be isolated from chromosomal DNA, which include an open reading frame encoding a protein, e.g. *G. oxydans* DSM 17078 STS proteins. A polynucleotide may include a polynucleotide sequence as shown in SEQ ID NO:1 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of STS proteins may exist within a population, e.g., the *Gluconobacter oxydans* population. Such genetic polymorphism in the STS 18 gene may exist among individuals within a population due to natural variation or in cells from different populations. Such natural variations can typically result in 1-5% variance in the nucleotide sequence of the STS 18 gene. Any and all such nucleotide variations and the resulting amino acid polymorphism in STS 18 are the result of natural variation and that do not alter the functional activity of STS proteins are intended to be within the scope of the invention.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides maybe used, for example, to prepare nucleic acids that have altered base-pairing abilities or increased resistance to nucleases.

The sequence information as provided herein should not be so narrowly construed as to require inclusion of erroneously identified bases. The specific sequences disclosed herein may be readily used to isolate the complete gene from a recombinant or non-recombinant microorganism capable of converting a given carbon source directly into Vitamin C, in particular *Gluconobacter oxydans*, preferably *Gluconobacter*

*oxydans* DSM 17078 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1, for example a fragment which may be used as a probe or primer such as for instance SEQ ID NO:3 or SEQ ID NO:4 or a fragment encoding a portion of a protein according to the invention. The nucleotide sequence determined from the cloning of the STS 18 gene allows for the generation of probes and primers designed for use in identifying and/or cloning other STS 18 family members, as well as STS 18 homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1 or a fragment or derivative thereof.

A nucleic acid molecule encompassing all or a portion of the nucleic acid sequence of SEQ ID NO:1 may be also isolated by the polymerase chain reaction (PCR) using synthetic oligonucleotide primers designed based upon the sequence information contained herein.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, may be used as hybridization probes or polymerase chain reaction (PCR) primers. Uses of the nucleic acid molecules of the present invention that do not encode a polypeptide having a STS 18 activity include, inter alia, (1) isolating the gene encoding the protein of the present invention, or allelic variants thereof from a cDNA library, e.g., from other organisms than *Gluconobacter oxydans* and (2) Northern blot analysis for detecting expression of mRNA of said protein in specific cells or (3) use in enhancing and/or improving the function or activity of homologous STS 18 genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *G. oxydans* STS 18 DNA of the invention which are also embraced by the present invention may be isolated based on their homology to the *G. oxydans* STS 18 nucleic acid disclosed herein using the *G. oxydans* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Also, nucleic acids encoding other STS 18 family members, which thus have a nucleotide sequence that differs from a nucleotide sequence according to SEQ ID NO:1, are within the scope of the invention. Moreover, nucleic acids encoding STS 18 proteins from different species which thus may have a nucleotide sequence which differs from a nucleotide sequence shown in SEQ ID NO:1 are within the scope of the invention.

The invention also relates to an isolated polynucleotide hybridisable under stringent conditions, preferably under highly stringent conditions, to a polynucleotide as of the present invention, such as for instance a polynucleotide shown in SEQ ID NO:1. Advantageously, such polynucleotide maybe obtained from a microorganism capable of converting a given carbon source directly into Vitamin C, in particular *Gluconobacter oxydans*, preferably *Gluconobacter oxydans* DSM 17078.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of stringent hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *G. oxydans* STS 18 protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting a given carbon source directly into Vitamin C, in particular other *Gluconobacter* species may be screened.

For example, *Gluconobacter* strains may be screened for homologous polynucleotides by Southern and/or Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule shown in SEQ ID NO:1 or a fragment or derivative thereof, may be isolated using standard molecular biology techniques and the sequence information provided herein. For example, using all or portion of the nucleic acid sequence shown in SEQ ID NO:1 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.accelrys.com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available at http://vega.igh.cnrs.fr/bin/align-guess.cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. See http://www.ncbi.nlm.nih.gov.

In another preferred embodiment, an isolated nucleic acid molecule of the invention comprises a nucleic acid molecule which is the complement of a nucleotide sequence as of the present invention, such as for instance the sequence shown in SEQ ID NO:1. A nucleic acid molecule, which is complementary to a nucleotide sequence disclosed herein, is one that is sufficiently complementary to a nucleotide sequence shown in SEQ ID NO:1 such that it may hybridize to said nucleotide sequence thereby forming a stable duplex.

In a further preferred embodiment, a nucleic acid of the invention as shown in SEQ ID NO:1 or the complement thereof contains at least one mutation leading to a gene product with modified function/activity. The at least one mutation may be introduced by methods described herein. In one aspect, the at least one mutation leads to a STS 18 protein whose function and/or activity compared to the wild type counterpart is enhanced or improved. Methods for introducing such mutations are well known in the art.

The term "increase" of activity as used herein encompasses increasing activity of one or more polypeptides in the producing organism, which in turn are encoded by the corresponding polynucleotides described herein. There are a number of methods available in the art to accomplish increase of activity of a given protein, in this case the STS 18 protein. In general, the specific activity of a protein may be increased or the copy number of the protein may be increased. The term increase of activity or equivalent expressions also encompasses the situation wherein STS 18 protein activity is introduced in a cell that did not contain this activity before, e.g. by introducing a gene encoding STS 18 in a cell that did not contain an equivalent of this gene before, or that could not express an active form of the corresponding protein before.

To facilitate such an increase, the copy number of the genes corresponding to the polynucleotides described herein may be increased. Alternatively, a strong promoter may be used to direct the expression of the polynucleotide. In another embodiment, the promoter, regulatory region and/or the ribosome binding site upstream of the gene can be altered to increase the expression. The expression may also be enhanced or increased by increasing the relative half-life of the messenger RNA. In another embodiment, the activity of the polypeptide itself may be increased by employing one or more mutations in the polypeptide amino acid sequence, which increase the activity. For example, altering the affinity of the polypeptide for its corresponding substrate may result in improved activity. Likewise, the relative half-life of the polypeptide may be increased. In either scenario, that being enhanced gene expression or increased specific activity, the improvement may be achieved by altering the composition of the cell culture media and/or methods used for culturing. "Enhanced expression" or "improved activity" as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are enhanced and/or improved. The activity of the STS 18 protein may also be enhanced by contacting the protein with a specific or general enhancer of its activity.

Another aspect of the invention pertains to vectors, containing a nucleic acid encoding a protein according to the invention or a functional equivalent or portion thereof. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome.

Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., STS 18 proteins, mutant forms of STS 18 proteins, fusion proteins and the like.

The recombinant expression vectors of the invention may be designed for expression of STS 18 proteins in a suitable microorganism. For example, a protein according to the invention may be expressed in bacterial cells such as strains belonging to the genera *Gluconobacter, Gluconacetobacter* or *Acetobacter*. Expression vectors useful in the present invention include chromosomal-, episomal- and virus-derived vectors e.g., vectors derived from bacterial plasmids, bacteriophage, and vectors derived from combinations thereof, such as those derived from plasmid and bacteriophage genetic elements, such as cosmids and phagemids.

The DNA insert may be operatively linked to an appropriate promoter, which may be either a constitutive or inducible promoter. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Vector DNA may be introduced into suitable host cells via conventional transformation or transfection techniques. As used herein, the terms "transformation", "transconjugation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid mediated transfection or electroporation. Suitable methods for transforming or transfecting host cells may be found in Sambrook, et al. (supra), Davis et al., Basic Methods in Molecular Biology (1986) and other laboratory manuals.

In order to identify and select cells which have integrated the foreign DNA into their genome, a gene that encodes a selectable marker (e.g., resistance to antibiotics) is generally introduced into the host cells along with the gene of interest. Preferred selectable markers include those that confer resistance to drugs, such as kanamycin, tetracycline, ampicillin and streptomycin. A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transfected with the introduced nucleic acid can be identified by drug selection (e.g. cells that have incorporated the selectable marker gene will survive, while the other cells die).

The invention provides also an isolated polypeptide having the amino acid sequence shown in SEQ ID NO:2 or an amino acid sequence obtainable by expressing a polynucleotide of the present invention, such as for instance a polynucleotide sequence shown in SEQ ID NO:1 in an appropriate host.

Polypeptides according to the invention may contain only conservative substitutions of one or more amino acids in the amino acid sequence represented by SEQ ID NO:2 or substitutions, insertions or deletions of non-essential amino acids. Accordingly, a non-essential amino acid is a residue that may be altered in the amino acid sequences shown in SEQ ID NO:2 without substantially altering the biological function. For example, amino acid residues that are conserved among the proteins of the present invention, are predicted to be particularly unamenable to alteration. Furthermore, amino acids conserved among the proteins according to the present invention and other STS 18 proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g. threonine, valine, isoleucine) and aromatic side chains (e.g., tyrosine, phenylalanine, tryptophan, histidine).

As mentioned above, the polynucleotides of the invention may be utilized in the genetic engineering of a suitable host cell to make it better and more efficient in the fermentation, for example in a direct fermentation process for Vitamin C.

According to the invention a genetically engineered/recombinantly produced host cell (also referred to as recombinant cell or transformed cell) carrying such a modified polynucleotide wherein the function of the linked protein is significantly modified in comparison to a wild-type cell such that the yield, production and/or efficiency of production of one or more fermentation products such as Vitamin C is improved. The host cell may be selected from a microorganism capable of directly producing one or more fermentation products such as for instance Vitamin C from a given carbon source, in particular *Gluconobacter oxydans*, preferably *G. oxydans* DSM 17078.

A "transformed cell" or "recombinant cell" is a cell into which (or into an ancestor of which) has been introduced, by means of recombinant DNA techniques, a nucleic acid according to the invention, or wherein the activity of the STS 18 protein has been increased and/or enhanced. Suitable host cells include cells of microorganisms capable of producing a given fermentation product, e.g., converting a given carbon source directly into Vitamin C. In particular, these include strains from the genera *Pseudomonas, Pantoea, Escherichia, Corynebacterium, Ketogulonicigenium* and acetic acid bacteria like e.g., *Gluconobacter, Acetobacter* or *Gluconacetobacter*, preferably *Acetobacter* sp., *Acetobacter aceti, Gluconobacter frateurii, Gluconobacter cerinus, Gluconobacter thailandicus, Gluconobacter oxydans*, more preferably *G. oxydans*, most preferably *G. oxydans* DSM 17078.

Improved gene expression may also be achieved by modifying the STS 18 gene, e.g., by introducing one or more mutations into the STS 18 gene wherein said modification leads to a STS 18 protein with a function which is significantly improved in comparison to the wild-type protein.

Therefore, in one other embodiment, the polynucleotide carrying the at least one mutation is derived from a polynucleotide as represented by SEQ ID NO:1 or equivalents thereof.

A mutation as used herein may be any mutation leading to a more functional or more stable polypeptide, e.g. more functional or more stable STS 18 gene products. This may include for instance an alteration in the genome of a microorganism, which improves the synthesis of STS 18 or leads to the expression of a STS 18 protein with an altered amino acid sequence whose function compared with the wild type counterpart having a non-altered amino acid sequence is improved and/or enhanced. The improvement may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a more functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout or suppress a repressor of the STS 18 gene of the present invention, i.e., wherein its repressor gene expression is artificially suppressed in order to improve the yield, productivity, and/or efficiency of production of the fermentation product when introduced into a suitable host cell. Methods of providing knockouts as well as microorganisms carrying such suppressed genes are well known in the art. The suppression of the repressor gene may be induced by deleting at least a part of the repressor gene or the regulatory region thereof. As used herein, "suppression of the gene expression" includes complete and partial suppression, as well as suppression under specific conditions and also suppression of the expression of either one of the two alleles.

The aforementioned mutagenesis strategies for STS 18 proteins may result in increased yields of a desired compound in particular Vitamin C. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated STS 18 nucleic acid and protein molecules such that the yield, productivity, and/or efficiency of production of a desired compound such as Vitamin C is improved.

In connection with the above process using a microorganism, in one aspect, the process of the present invention leads to yields of Vitamin C which are in general at least about more than 5.7 µl, such as 10 g/l, 20 g/l, 50 g/l, 100 µl, 200 g/l, 300 g/l, 400 g/l or more than 600 g/l. In one embodiment, the yield of Vitamin C produced by the process of the present invention is in the range of from about more than 5.7 to about 600 µl. The yield of Vitamin C refers to the concentration of Vitamin C in the harvest stream coming directly out of the production vessel, i.e. the cell-free supernatant comprising the Vitamin C.

In one aspect of the invention, microorganisms (in particular from the genera of *Gluconobacter, Gluconacetobacter* and *Acetobacter*) are provided that are able to directly produce Vitamin C from a suitable carbon source like D-sorbitol and/or L-sorbose. When measured for instance in a resting cell method after an incubation period of 20 hours, these organisms were found to be able to produce Vitamin C directly from D-sorbitol or L-sorbose, even up to a level of 280 mg/l and 670 mg/l respectively. In another aspect of the invention, a microorganism is provided capable of directly producing Vitamin C in quantities of 300 mg/l when starting from D-sorbitol or more or 800 mg/l or more when starting from L-sorbose, respectively when for instance measured in a resting cell method after an incubation period of 20 hours. Such may be achieved by increasing the activity of a STS polypeptide, preferably a STS 18 polypeptide. The yield of Vitamin C produced from D-sorbitol may even be as high as 400, 600, 1000 mg/l or even exceed 1.5, 2, 4, 10, 20, 50 g/l. The yield of Vitamin C produced from L-sorbose may even be as high as 1000 mg/l or even exceed 1.5, 2, 4, 10, 20, 50 g/l. Preferably, these amounts of Vitamin C can be achieved when measured by resting cell method after an incubation period of 20 hours.

As used herein, measurement in a "resting cell method" comprises (i) growing the cells by means of any method well know to the person skilled in the art, (ii) harvesting the cells from the growth broth, and (iii) incubating the harvested cells in a medium containing the substrate which is to be converted into the desired product, e.g. Vitamin C, under conditions where the cells do not grow any longer, i.e. there is no increase in the amount of biomass during this so-called conversion step.

The recombinant microorganism carrying e.g. a modified STS 18 gene and which is able to produce the fermentation product in significantly higher yield, productivity, and/or efficiency may be cultured in an aqueous medium supplemented with appropriate nutrients under aerobic conditions as described above.

The nucleic acid molecules, polypeptides, vectors, primers, and recombinant microorganisms described herein may be used in one or more of the following methods: identification of *Gluconobacter oxydans* and related organisms; mapping of genomes of organisms related to *Gluconobacter oxydans*; identification and localization of *Gluconobacter oxydans* sequences of interest; evolutionary studies; determination of STS 18 protein regions required for function; modulation of a STS 18 protein activity or function; modulation of the activity of a STS pathway; and modulation of cellular production of a desired compound, such as Vitamin C.

The invention provides methods for screening molecules which modulate the activity of a STS 18 protein, either by interacting with the protein itself or a substrate or binding partner of the STS 18 protein, or by modulating the transcription or translation of a STS 18 nucleic acid molecule of the invention. In such methods, a microorganism expressing one or more STS 18 proteins of the invention is contacted with one or more test compounds, and the effect of each test compound on the activity or level of expression of the STS 18 protein is assessed.

The biological, enzymatic or other activity of STS proteins can be measured by methods well known to a skilled person, such as, for example, by incubating a membrane fraction containing the STS protein with the radioactively marked sugar or sugar alcohol which can be actively transported by the STS protein. The incorporation of radioactivity into the cell mass is directly proportional to the activity of the transporter. Thus, for example, the activity of a transporter can be measured in an assay where intact cells containing the specific transporter are incubated in the presence of phosphate buffer at pH 6 and the radioactively marked carbon source such as e.g. glucose. The rate of assimilation of radioactive carbon source such as e.g. glucose by the cells can be measured by methods known to the skilled person, and is directly proportional to the STS protein activity present in the membrane fraction.

It may be evident from the above description that the fermentation product of the methods according to the invention may not be limited to Vitamin C alone. The "desired compound" or "fermentation product" as used herein may be any natural product of *Gluconobacter oxydans*, which includes the final products and intermediates of biosynthesis pathways, such as for example L-sorbose, L-sorbosone, D-gluconate, 2-keto-D-gluconate, 5-keto-D-gluconate, 2,5-diketo-D-gluconate and 2-keto-L-gluconate (2-KGA), in particular the biosynthetic generation of Vitamin C.

Thus, the present invention is directed to the use of a polynucleotide, polypeptide, vector, primer and recombinant microorganism as described herein in the production of Vitamin C, i.e., the direct conversion of a carbon source into Vitamin C. In a preferred embodiment, a modified polynucleotide, polypeptide, vector and recombinant microorganism as described herein is used for improving the yield, productivity, and/or efficiency of the production of Vitamin C.

The terms "production" or "productivity" are art-recognized and include the concentration of the fermentation product (for example, Vitamin C) formed within a given time and a given fermentation volume (e.g., kg product per hour per liter). The term "efficiency of production" includes the time required for a particular level of production to be achieved (for example, how long it takes for the cell to attain a particular rate of output of a fermentation product). The term "yield" is art-recognized and includes the efficiency of the conversion of the carbon source into the product (i.e., Vitamin C). This is generally written as, for example, kg product per kg carbon source. By "increasing the yield and/or production/productivity" of the compound it is meant that the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise either be unable to pass or be passed inefficiently.

Vitamin C as used herein may be any chemical form of L-ascorbic acid found in aqueous solutions, such as for instance undissociated, in its free acid form or dissociated as an anion. The solubilized salt form of L-ascorbic acid may be characterized as the anion in the presence of any kind of cations usually found in fermentation supernatants, such as for instance potassium, sodium, ammonium, or calcium. Also included may be isolated crystals of the free acid form of L-ascorbic acid. On the other hand, isolated crystals of a salt form of L-ascorbic acid are called by their corresponding salt name, i.e. sodium ascorbate, potassium ascorbate, calcium ascorbate and the like.

In one preferred embodiment, the present invention is related to a process for the production of Vitamin C wherein a nucleotide according to the invention or a modified polynucleotide sequence as described above is introduced into a suitable microorganism, the recombinant microorganism is cultured under conditions that allow the production of Vitamin C in high productivity, yield, and/or efficiency, the produced fermentation product is isolated from the culture medium and optionally further purified.

This invention is further illustrated by the following examples which should not be construed as limiting. The contents of all references, patent applications, patents and published patent applications, cited throughout this application are hereby incorporated by reference.

EXAMPLES

Example 1

Preparation of Chromosomal DNA and Amplification of DNA Fragment by PCR

Chromosomal DNA of *Gluconobacter oxydans* DSM 17078 was prepared from the cells cultivated at 30° C. for 1 day in mannitol broth (MB) liquid medium consisting of 25 µl mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:3) and Pr (SEQ ID NO:4). For the reaction, the Expand High Fidelity PCR kit (Roche Diagnostics) and 10 ng of the chromosomal DNA was used in total volume of 100 µl according to the supplier's instruction to have the PCR product containing STS 18 DNA sequence (SEQ ID NO:1). The PCR product was recovered from the reaction and its correct sequence confirmed.

Example 2

Overexpression of the STS 18 Gene in *G. oxydans* DSM 17078

To upregulate the expression of the STS 18 gene, an overexpression system using an integrative construct may be used. Herein, the STS 18 gene is fused to a strong constitutive promoter, and the construct is then introduced into *G. oxydans* DSM 17078. The overexpression of the STS 18 gene may be determined through standard methods known to those skilled in the art, such as transcript analysis using Northern Blot, RT-PCR or other technology, protein expression determination using Western Blot, two-dimensional gel electrophoresis, protein activity determination using specific enzyme assays or through direct measurement of product formation or substrate conversion.

The promoter can be any promoter that exhibits strong constitutive activity in *Gluconobacter oxydans* such as the tufB promoter from *Escherichia coli*, the tufB promoter from *Gluconobacter oxydans*, the dnaA promoter from *Gluconobacter oxydans*, or the sndh promoter from *Gluconobacter oxydans*.

For the overexpression of the STS 18 gene, the promoter of the STS 18 gene may be replaced by the strong constitutive modified $P_{sndh}$ promoter (SEQ ID NO:5). In order to achieve this, a DNA fragment is built up by Long Flanking Homology (LFH)-PCR consisting of 500-bp of the upstream region of the STS 18 gene, a kanamycin-resistance cassette, the $P_{sndh}$-promoter fused to a modified ribosome binding site and the first 500-bp of the STS 18 gene. In order to construct the DNA fragment, firstly the single parts are amplified by PCR using the GC-rich PCR kit (Roche Molecular Biochemicals). The STS 18 DNA upstream region is amplified using primer pair STS 18US+1 (SEQ ID NO:6) and KmSTS 18US-1 (SEQ ID NO:7) containing complementary kanamycin-resistance cassette overhang sequence at 5'-end. The $P_{sndh}$ promoter fragment is amplified using primer pair KmPsndh+1 (SEQ ID NO:8) containing complementary kanamycin-resistance cassette overhang sequence at 5'-end and STS 18Psndh-1 (SEQ ID NO:9) containing complementary STS 18 DNA overhang sequence at 5'-end. The first 500-bp of the STS 18 gene is amplified using primer pair PsndhSTS 18+1 (SEQ ID NO:10) containing complementary $P_{sndh}$ promoter overhang sequence at 5'-end and STS 18-1 (SEQ ID NO:11). In these cases G. oxydans DSM 17078 genomic DNA is used as a template. The kanamycin-resistance cassette is amplified using plasmid pUC4K (Amersham Bioscience, accession No. X06404) as a template and primer pair Km+1 (SEQ ID NO:12) and Km-1 (SEQ ID NO:13). The PCR conditions consist of 35 cycles of denaturation at 94° C. for 30 sec, annealing at 50° C. for 30 sec and extension at 72° C. for 1 min. The individual PCR fragments are gel-purified, mixed and re-amplified using the primer pair STS 18US+1/STS 18-1 to amplify a full length product whereby the $P_{sndh}$ promoter is inserted upstream of the STS 18 gene. The PCR reaction conditions for the second round reaction consist of 94° C., 2 min, then 10 cycles of [94° C., 30 sec, 63° C., 30 sec, 68° C., 6 min], followed by 20 cycles of [94° C., 30 sec, 63° C., 30 sec, 68° C., 6 min with an additional 20 sec per cycle] and a final extension at 68° C. for 10 min.

The PCR product is transformed directly into competent G. oxydans DSM 17078 cells and transformants are selected on mannitol broth agar medium containing kanamycin to a final concentration of 50 µg ml$^{-1}$. Several putative transformants are observed of which several are then analyzed by PCR using primer pair STS 18US+1/STS 18-1 to verify that the DNA fragment has inserted into the genome via a double crossover. Strains showing the correct size PCR product have the PCR product sequenced. Strains with the correct sequence are named G. oxydans DSM 17078-STS 18up1 and G. oxydans DSM 17078-STS 18up2.

Example 3

Production of Vitamin C from D-Sorbitol Using Resting Cells

Cells of G. oxydans DSM 17078, G. oxydans DSM 17078-STS 18up1 and G. oxydans DSM 17078-STS 18up2 are grown at 27° C. for 3 days on No. 3BD agar medium containing 70 g/l D-sorbitol, 0.5 g/l glycerol, 7.5 g/l yeast extract (Difco), 2.5 g/l MgSO$_4$.7H$_2$O, 10 g/l CaCO$_3$ and 18 g/l agar (Difco).

Cells are scraped from the agar plates, suspended in distilled water and used for resting cell reactions conducted at 30° C. with shaking at 220 rpm. A series of reactions (0.5 ml reaction mixture in 5 ml reaction tubes) are carried out with 2% D-sorbitol in reaction mixtures further containing 0.3% NaCl, and 1% CaCO$_3$ and is incubated with cells at a final concentration of OD$_{600}$=10. After an incubation period of 20 hours, samples of the reaction mixtures are analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase is 0.004 M sulfuric acid, and the flow rate was 0.6 ml/min. Two signals are recorded using an UV detector (wavelength 254 nm) in combination with a refractive index detector. In addition, the identification of the L-ascorbic acid is done using an amino-column (YMC-Pack Polyamine-II, YMC, Inc., Kyoto, Japan) with UV detection at 254 nm. The mobile phase is 50 mM NH$_4$H$_2$PO$_4$ and acetonitrile (40:60).

An Agilent Series 1100 HPLC-mass spectrometry (MS) system is used to identify L-ascorbic acid. The MS is operated in positive ion mode using the electrospray interface. The separation is carried out using a LUNA-C8(2) column (100× 4.6 mm) (Phenomenex, Torrance, USA). The mobile phase is a mixture of 0.1% formic acid and methanol (96:4). L-Ascorbic acid elutes with a retention time of 3.1 minutes. The identity of the 1-ascorbic acid is confirmed by retention time and the molecular mass of the compound.

The supernatants of the reaction mixtures incubated with cells of G. oxydans DSM 17078-STS 18up1 and G. oxydans DSM 17078-STS 18up2 contain at least 20% more Vitamin C than the supernatant of the reaction mixture incubated with cells of G. oxydans DSM 17078.

Example 4

Presence of the STS 18 Gene and Equivalents in Other Organisms

The presence of SEQ ID NO:1 and/or equivalents in other organisms than the ones disclosed herein before, e.g. organisms as mentioned in Table 1, may be determined by a simple DNA hybridization experiment.

Strains of Acetobacter aceti subsp. xylinum IFO 13693 and IFO 13773 are grown at 27° C. for 3 days on No. 350 medium containing 5 g/l Bactopeptone (Difco), 5 g/l yeast extract (Difco), 5 g/l glucose, 5 g/l mannitol, 1 g/l MgSO$_4$.7H$_2$O, 5 ml/i ethanol, and 15 g/l agar. All other Acetobacter, Gluconacetobacter and all Gluconobacter strains are grown at 27° C. for 3 days on mannitol broth (MB) agar medium containing 25 g/l mannitol, 5 g/l yeast extract (Difco), 3 g/l Bactopeptone (Difco), and 18 g/l agar (Difco). E. coli K-12 is grown on Luria Broth agar medium. The other strains are grown on medium recommended by the suppliers or according to methods known in the art. Genomic DNA is extracted as described by e.g. Sambrook et al., 1989, "Molecular Cloning: A Laboratory Manual/Second Edition", Cold Spring Harbor Laboratory Press) from a suitable organism as, e.g. mentioned in Table 1.

Genomic DNA preparations are digested with restriction enzymes such as EcoRI or HindIII, and 1 µg of the DNA fragments are separated by agarose gel electrophoresis (1% agarose). The gel is treated with 0.25 N HCl for 15 min and then 0.5 N NaOH for 30 min, and then blotted onto nitrocellulose or a nylon membrane with Vacuum Blotter Model 785 (BIO-RAD Laboratories AG, Switzerland) according to the instruction of the supplier. The resulting blot is then brought into contact/hybridized with a solution wherein the probe, such as e.g. a DNA fragment with SEQ ID NO:1 sequence or a DNA fragment containing the part or whole of the SEQ ID NO:1 sequence to detect positive DNA fragment(s) from a test organism. A DIG-labeled probe, e.g. SEQ ID NO:1, maybe prepared according to Example 1 by using the PCR-DIG labeling kit (Roche Diagnostics) and a set of primers, SEQ ID NO:3 and SEQ ID NO:4. A result of such a blot is depicted in Table 1.

The hybridization may be performed under stringent or highly stringent conditions. A preferred, non-limiting example of such conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C. Highly stringent conditions include, for example, 2 h to 4 days incubation at 42° C. in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 min in 2×SSC and 0.1% SDS at room temperature and then washing twice for 15-30 min in 0.5×SSC and 0.1% SDS or 0.1×SSC and 0.1% SDS at 65-68° C. To detect DNA fragments with lower identity to the probe DNA, final washing steps can be done at lower temperatures such as 50-65° C. and for shorter washing time such as 1-15 min.

The genes corresponding to the positive signals within the respective organisms shown in Table 1 can be cloned by a PCR method well known in the art using genomic DNA of such an organism together with a suitable primer set, such as e.g. SEQ ID NO:3 and SEQ ID NO:4 under conditions as described in Example 1 or as follows: 5 to 100 ng of genomic DNA is used per reaction (total volume 50 µl). Expand High Fidelity PCR system (Roche Diagnostics) can be used with reaction conditions consisting of 94° C. for 2 min; 30 cycles of (i) denaturation step at 94° C. for 15 sec, (ii) annealing step at 60° C. for 30 sec, (iii) synthesis step at 72° C. for 0.5 to 5 min depending to the target DNA length (1 min/1 kb); extension at 72° C. for 7 min. Alternatively, one can perform a PCR with degenerate primers, which can be synthesized based on SEQ ID NO:2 or amino acid sequences as consensus sequences selected by aligning several amino acid sequences obtained by a sequence search program such as BLASTP (or BLASTX when nucleotide sequence is used as a "query sequence") to find proteins having a similarity to the protein of SEQ ID NO:2. For PCR using degenerate primers, temperature of the second annealing step (see above) can be lowered to 55° C., or even to 50-45° C. A result of such an experiment is shown in Table 1.

Samples of the PCR reactions are separated by agarose gel electrophoresis and the bands are visualized with a transilluminator after staining with e.g. ethidium bromide, isolated from the gel and the correct sequence is confirmed.

Consensus sequences mentioned above might be amino acid sequences belonging to certain categories of several protein domain/family databases such as PROSITE (database of protein families and domains), COGs (Cluster of Ortholog Groups), CDD (Conserved Domain Databases), pfam (large collection of multiple sequence alignments and hidden Markov models covering many common protein domains and families). Once one can select certain protein with identical/similar function to the protein of this invention from proteins containing domain or family of such databases, corresponding DNA encoding the protein can be amplified by PCR using the protein sequence or its nucleotide sequence when it is available in public databases. Following organisms may further provide genes, which can be used as an alternative gene of this invention: *Xanthomonas campestris* pv. *campestris* ATCC 33913, *Xanthomonas oryzae* pv. *oryzae* KACC 10331, *Agrobacterium tumefaciens* C58, *Bradyrhizobium japonicum* USDA 110, *Sinorhizobium meliloti* 1021 or *Ralstonia solanacearum* GMI 1000.

Example 5

Overexpression of the STS 18 Gene and Equivalents from Other Organisms for Production of Vitamin C In order to improve Vitamin C production in a suitable microorganism which is capable to directly produce Vitamin C from a given substrate, the STS 18 gene and equivalents as, e.g. a PCR product obtained in Example 4, referred to herein as gene X, can be used in an overexpression system according to Example 2 or can be cloned into pCR2.1-TOPO (Invitrogen, Carlsbad, Calif., USA) and used to transform *E. coli* TG1 to have a Apr transformant carrying pCR2.1-TOPO-gene X, i.e. carrying a PCR product obtained in Example 4. The insert is amplified with a set of primers, PfNdeI [SEQ ID NO:3 with CCCAT at the 5'-end] and PrHindIII [SEQ ID NO:4 with CCAAGCTT at the 5'-end], by PCR. Resulting PCR product is digested with NdeI and HindIII and the fragment is inserted together with PcrtE-SD (Shine-Dalgarno) fragment (WO 02/099095) digested with XhoI and NdeI into pVK100 (ATCC 37156) between the sites of XhoI and HindIII. *E. coli* TG1 is transformed with the ligation product to have Tc$^r$ transformant carrying plasmid pVK-PcrtE-SD-gene X, which is then used to transform a suitable host, e.g. *G. oxydans* DSM 17078 by electroporation to have e.g. Tc$^r$ *G. oxydans* DSM 17078/pVK-PcrtE-SD-gene X.

Production of Vitamin C using the recombinant cells of e.g. *G. oxydans* strains DSM 17078 and the corresponding wild-type strain are performed according to Example 3.

In the resting cell reaction with 1% L-sorbosone as the substrate, the recombinant cells can produce at least more than 20% Vitamin C compared to the wild-type strain.

TABLE 1

Equivalents of the STS 18 gene in other organisms.

| Strain | Signal 1 | Signal 2 | Signal 3 |
| --- | --- | --- | --- |
| *G. oxydans* DSM 17078 | ++++ | + | + |
| *G. oxydans* IFO 3293 | ++++ | + | + |
| *G. oxydans* IFO 3292 | +++ | + | + |
| *G. oxydans* ATCC 621H | +++ | + | + |
| *G. oxydans* IFO 12528 | +++ | + | + |
| *G. oxydans* G 624 | +++ | + | + |
| *G. oxydans* T-100 | +++ | + | + |
| *G. oxydans* IFO 3291 | +++ | + | + |
| *G. oxydans* IFO 3255 | +++ | + | + |
| *G. oxydans* ATCC 9937 | +++ | + | + |
| *G. oxydans* IFO 3244 | +++ | + | + |
| *G. cerinus* IFO 3266 | +++ | + | + |
| *G. frateurii* IFO 3260 | +++ | + | + |
| *G. oxydans* IFO 3287 | +++ | + | + |
| *Acetobacter aceti* subsp. *orleanus* IFO 3259 | + | − | + |
| *Acetobacter aceti* subsp. *xylinum* IFO 13693 | + | − | + |
| *Acetobacter aceti* subsp. *xylinum* IFO 13773 | + | − | + |
| *Acetobacter sp.* ATCC 15164 | + | − | + |
| *G. thailandicus* NBRC 100600 | +++ | + | + |
| *Gluconacetobacter liquefaciens* ATCC 14835 | ++ | + | + |
| *Gluconacetobacter polyoxogenes* NBI 1028 | + | + | + |
| *Gluconacetobacter diazotrophicus* ATCC 49037 | + | + | + |
| *Gluconacetobacter europaeus* DSM 6160 | + | + | + |
| *Acetobacter aceti* 1023 | + | − | + |
| *Acetobacter pasteurianus* NCI 1193 | + | − | + |
| *Pseudomonas putida* ATCC 21812 | − | − | + |
| *Pseudomonas aeruginosa* PAO1 | + | − | + |
| *Pseudomonas fluorescens* DSM 50106 | + | − | + |

TABLE 1-continued

Equivalents of the STS 18 gene in other organisms.

| Strain | Signal 1 | Signal 2 | Signal 3 |
|---|---|---|---|
| *Pseudomonas syringae* B728a | + | − | + |
| *Paracoccus denitrificans* strain Pd1222 | − | − | + |
| *Rhodopseudomonas palustris* CGA009 | − | − | + |
| *Pantoea citrea* 1056R | − | − | − |
| *E. coli* | − | − | − |
| *Saccharomyces cerevisiae* | − | − | − |
| *Aspergillus niger* | − | − | − |
| Mouse | − | − | − |

Signal 1: Detection of DNA on a blot with genomic DNA of different strains and SEQ ID NO: 1 as labeled probe.
Signal 2: Detection of DNA of different strains in a PCR reaction using primer pair SEQ ID NO: 3 and SEQ ID NO: 4.
Signal 3: Detection of DNA of different strains in a PCR reaction using degenerate primers. For more explanation refer to the text.

The invention claimed is:

1. A process of using a polynucleotide or a vector containing the polynucleotide for production of Vitamin C, comprising overexpressing said polynucleotide or said vector, wherein said polynucleotide comprises a nucleotide sequence selected from the group consisting of:
   (a) nucleotide sequences encoding a polypeptide comprising SEQ ID NO: 2;
   (b) nucleotide sequences comprising SEQ ID NO: 1;
   (c) nucleotide sequences obtainable by nucleic acid amplification using genomic DNA from *Gluconobacter*, *Acetobacter* or *Gluconoacetobacter* as a template and primers comprising SEQ ID NO: 3 and SEQ ID NO: 4 and encoding protein having activity of a periplasmic sorbitol binding protein; and
   (d) nucleotide sequences the complementary strand of which hybridizes under highly stringent conditions to a nucleotide sequence as defined in (a) or (b) and which encode a periplasmic sorbitol binding protein, wherein said highly stringent conditions comprise hybridization at about 42° C. for about 2 to 4 days followed by one or more washes in 2×SSC, 0.1% SDS at room temperature and one or more washes in 0.5×SSC, 0.1% SDS or 0.1×SSC, 0.1% SDS at about 65 to about 68° C.; and wherein the production of Vitamin C is increased by at least 20% compared to a process wherein said polynucleotide or said vector is not overexpressed.

2. The process according to claim 1, wherein the polynucleotide is operatively linked to expression control sequences and transferred into a microorganism.

3. The process according to claim 2, wherein the expression control sequences comprise a regulation-, and/or promoter-, and/or terminator sequence and wherein at least one of these sequences is altered in such a way that it leads to an improved yield and/or efficiency of production of Vitamin C produced by said microorganism.

4. The process according to claim 3, wherein the expression control sequences comprise a regulation-, and/or promoter-, and/or terminator sequence and wherein at least one of these sequences is altered in such a way that it leads to an increased and/or improved activity of a sugar transporter and/or sugar alcohol transporter.

5. A process for production of Vitamin C using a microorganism into which has been introduced a polynucleotide or a vector containing the polynucleotide for production of Vitamin C, wherein said polynucleotide comprises a nucleotide sequence selected from the group consisting of:
   (i) nucleotide sequences encoding a polypeptide comprising SEQ ID NO: 2;
   (ii) nucleotide sequences comprising SEQ ID NO: 1;
   (iii) nucleotide sequences obtainable by nucleic acid amplification using genomic DNA from *Gluconobacter*, *Acetobacter* or *Gluconoacetobacter* as a template and primers comprising SEQ ID NO: 3 and SEQ ID NO: 4 and encoding protein having activity of a periplasmic sorbitol binding protein; and
   (iv) nucleotide sequences the complementary strand of which hybridizes under highly stringent conditions to a nucleotide sequence as defined in (i) or (ii) and which encode a periplasmic sorbitol binding protein, wherein said highly stringent conditions comprise hybridization at about 42° C. for about 2 to 4 days followed by one or more washes in 2×SSC, 0.1% SDS at room temperature and one or more washes in 0.5×SSC, 0.1% SDS or 0.1×SSC, 0.1% SDS at about 65 to about 68° C.;
   wherein said process comprises:
   (a) cultivating said microorganism in a aqueous nutrient medium under conditions such that Vitamin C from D-sorbitol or L-sorbose is produced by direct fermentation and
   (b) optionally isolating Vitamin C as a fermentation product.

6. The process according to claim 5, wherein said polynucleotide comprises a nucleotide sequence encoding a polypeptide comprising SEQ ID NO: 2.

7. The process according to claim 5, wherein said polynucleotide comprises a nucleotide sequence obtainable by nucleic acid amplification using genomic DNA from *Gluconobacter, Acetobacter* or *Gluconoacetobacter* as a template and primers comprising SEQ ID NO: 3 and SEQ ID NO: 4 and which encodes a protein having activity of a periplasmic sorbitol binding protein.

8. The process according to claim 5, wherein said polynucleotide comprises a nucleotide sequence the complementary strand of which hybridizes under highly stringent conditions to SEQ ID NO: 1 and which encodes a periplasmic sorbitol binding protein, wherein said highly stringent conditions comprise hybridization at about 42° C. for about 2 to 4 days followed by one or more washes in 2×SSC, 0.1% SDS at room temperature and one or more washes in 0.5×SSC, 0.1% SDS or 0.1×SSC, 0.1% SDS at about 65 to about 68° C.

9. The process according to claim 5, wherein said microorganism is selected from acetic acid bacteria.

10. The process according to claim 5, wherein said microorganism is selected from the group consisting of *Gluconobacter, Acetobacter*, and *Gluconacetobacter*.

11. The process according to claim 5, wherein said microorganism is selected from the group consisting of *Acetobacter* sp., *Acetobacter aceti, Gluconobacter frateurii, Gluconobacter cerinus, Gluconobacter thailandicus*, and *Gluconobacter oxydans*.

12. The process according to claim 5, wherein said microorganism is selected from the group consisting of *Gluconobacter oxydans* and *Gluconobacter oxydans* DSM 17078.

13. The process according to claim 5 further comprising prior to (a), obtaining said microorganism by transfection with a polynucleotide or a vector comprising the polynucleotide.

14. The process according to claim 5, wherein Vitamin C is produced from D-sorbitol in quantities of 300 mg/l or more when measured in a resting cell method after an incubation period of 20 hours.

15. The process according to claim 5, wherein Vitamin C is produced from L-sorbose in quantities of 800 mg/l or more.

* * * * *

SEQUENCE LISTING

```
<160> NUMBER OF SEQ ID NOS: 4

<210> SEQ ID NO 1
<211> LENGTH: 1329
<212> TYPE: DNA
<213> ORGANISM: Gluconobacter oxydans DSM 17078

<400> SEQUENCE: 1
atgtcccgtc tcaaagccac acacacagcc atctgcactc tcgcccttct gctcacgggc      60
tccgccctgt ccagcgccga agccgccgga acgctgacga tcgccaccgt caacaacggc     120
gacatgatcg tcatgcggca gctttcccag gagtttgaga aggcccatcc ggacattcac     180
ctgaactggg tcacgctgga agaaaacgtc ctgcgtcagc gcgtcacgac cgatatcgcc     240
atgaaaaccg gtcagttcga tgtcgtgacc atcggcaact acgaagtgcc gatctgggcc     300
aagcagggct ggcttaccga actcaagccg gacgccacct atgacgtgaa cgacatcctg     360
ccctccgtcc gcgacagcct gacaacagat ggcaagctct atgccctgcc gttctacgcc     420
gaaagcgtca tgacctatta tcgcaaggac ctgttccaaa aggccgggct gacgatgccg     480
gacgcgccca cctacgacca gatccgccag ttcgccgaca agatcacgga caagggcaat     540
caggtctatg gtatctgcct gcgcggcaag ccgggctggg gcgagaacat ggcgtatatc     600
tcgtcgctcg ccaacacgtt cggcgctcag tggtttgaca tgtcctggaa gccgaccatg     660
acatccgatg cgtggaaagc gaccctgaac tggtacgtct cggctctgaa ggctgacggt     720 cctccggggtg cgacatccaa tggcttcaac gagaacctgg ccctgttcgc cagcggtcat     780
tgcgggatct ggattgattc caccgtcgca ggcgggctgc tgttcgatcc caaacagtcc     840
caggttgcgg acaaagtcgg tttcgcttcc tcccccaagg gtccttacgg caaaggcccg     900
acctggctgt ggagctggag cctcgccgtc ccgtcagct cccatcagag cgcagatgcc     960
cagaccttca ttacgtgggc aacgtccaag gactacgtga aactggtcgc cgcacagaaa    1020
ggctgggtcg ccgttccggc cggaacccgc gcctccacct atgccgcgcc ggaatacgtc    1080
aaggcagcgc ccttcgcttc cttcgtgctg aacgccatca gacggctga tccgaacggc    1140 ccgaccgccc agccgcgtcc ctataccggt gcgcagttcg tcggcatccc ggaattccag    1200
gccatcggca cacaggtcgg ccagaccgtt gccgcgaccc tgtccgatca gatgaccgtc    1260
gatcaggccc tgacctccgc ccaggcttcg atcacccgcg cgctccgcca gtccggccgc    1320
gcgcgataa                                                           1329

<210> SEQ ID NO 2
```

<211> LENGTH: 442
<212> TYPE: PRT
<213> ORGANISM: Gluconobacter oxydans DSM 17078

<400> SEQUENCE: 2

```
Met Ser Arg Leu Lys Ala Thr His Thr Ala Ile Cys Thr Leu Ala Leu
1               5                   10                  15

Leu Leu Thr Gly Ser Ala Leu Ser Ser Ala Glu Ala Ala Gly Thr Leu
            20                  25                  30

Thr Ile Ala Thr Val Asn Asn Gly Asp Met Ile Val Met Arg Gln Leu
        35                  40                  45

Ser Gln Glu Phe Glu Lys Ala His Pro Asp Ile His Leu Asn Trp Val
50                  55                  60

Thr Leu Glu Glu Asn Val Leu Arg Gln Arg Val Thr Thr Asp Ile Ala
65                  70                  75                  80

Met Lys Thr Gly Gln Phe Asp Val Val Thr Ile Gly Asn Tyr Glu Val
                85                  90                  95

Pro Ile Trp Ala Lys Gln Gly Trp Leu Thr Glu Leu Lys Pro Asp Ala
            100                 105                 110

Thr Tyr Asp Val Asn Asp Ile Leu Pro Ser Val Arg Asp Ser Leu Thr
        115                 120                 125

Thr Asp Gly Lys Leu Tyr Ala Leu Pro Phe Tyr Ala Glu Ser Val Met
    130                 135                 140

Thr Tyr Arg Lys Asp Leu Phe Gln Lys Ala Gly Leu Thr Met Pro
145                 150                 155                 160

Asp Ala Pro Thr Tyr Asp Gln Ile Arg Gln Phe Ala Asp Lys Ile Thr
                165                 170                 175

Asp Lys Gly Asn Gln Val Tyr Gly Ile Cys Leu Arg Gly Lys Pro Gly
            180                 185                 190

Trp Gly Glu Asn Met Ala Tyr Ile Ser Ser Leu Ala Asn Thr Phe Gly
        195                 200                 205

Ala Gln Trp Phe Asp Met Ser Trp Lys Pro Thr Met Thr Ser Asp Ala
    210                 215                 220

Trp Lys Ala Thr Leu Asn Trp Tyr Val Ser Ala Leu Lys Ala Asp Gly
225                 230                 235                 240

Pro Pro Gly Ala Thr Ser Asn Gly Phe Asn Glu Asn Leu Ala Leu Phe
                245                 250                 255

Ala Ser Gly His Cys Gly Ile Trp Ile Asp Ser Thr Val Ala Gly Gly
            260                 265                 270

Leu Leu Phe Asp Pro Lys Gln Ser Gln Val Ala Asp Lys Val Gly Phe
        275                 280                 285

Ala Ser Ser Pro Lys Gly Pro Tyr Gly Lys Gly Pro Thr Trp Leu Trp
    290                 295                 300

Ser Trp Ser Leu Ala Val Pro Val Ser Ser His Gln Ser Ala Asp Ala
305                 310                 315                 320

Gln Thr Phe Ile Thr Trp Ala Thr Ser Lys Asp Tyr Val Lys Leu Val
                325                 330                 335

Ala Ala Gln Lys Gly Trp Val Ala Val Pro Ala Gly Thr Arg Ala Ser
            340                 345                 350

Thr Tyr Ala Ala Pro Glu Tyr Val Lys Ala Ala Pro Phe Ala Ser Phe
        355                 360                 365

Val Leu Asn Ala Ile Lys Thr Ala Asp Pro Asn Gly Pro Thr Ala Gln
    370                 375                 380

Pro Arg Pro Tyr Thr Gly Ala Gln Phe Val Gly Ile Pro Glu Phe Gln
385                 390                 395                 400
```

```
Ala Ile Gly Thr Gln Val Gly Gln Thr Val Ala Ala Thr Leu Ser Asp
                405                 410                 415

Gln Met Thr Val Asp Gln Ala Leu Thr Ser Ala Gln Ala Ser Ile Thr
                420                 425                 430

Arg Ala Leu Arg Gln Ser Gly Arg Ala Arg
            435                 440

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgtcccgtc tcaaagccac                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttatcgcgcg cggccggact                                              20
```